United States Patent
Difato et al.

(10) Patent No.: US 10,655,147 B2
(45) Date of Patent: May 19, 2020

(54) METHOD FOR THE OPTOINJECTION OF EXOGENOUS MATERIAL INTO A BIOLOGICAL CELL

(71) Applicant: Fondazione Istituto Italiano di Tecnologia, Genoa (IT)

(72) Inventors: Francesco Difato, Genoa (IT); Alessandro Soloperto, Genoa (IT); Gemma Palazzolo, Genoa (IT)

(73) Assignee: Fondazione Istituto Italiano di Tecnologia, Genoa (IT)

( * ) Notice: Subject to any disclaimer, the term of this patent is extended or adjusted under 35 U.S.C. 154(b) by 147 days.

(21) Appl. No.: 16/067,217

(22) PCT Filed: Dec. 20, 2016

(86) PCT No.: PCT/IB2016/057829
§ 371 (c)(1),
(2) Date: Jun. 29, 2018

(87) PCT Pub. No.: WO2017/115220
PCT Pub. Date: Jul. 6, 2017

(65) Prior Publication Data
US 2019/0017071 A1    Jan. 17, 2019

(30) Foreign Application Priority Data
Dec. 30, 2015  (IT) .................. 102015888892

(51) Int. Cl.
*C12N 15/87* (2006.01)
*B23K 26/04* (2014.01)
*B23K 26/06* (2014.01)
*B23K 26/0622* (2014.01)
*C12M 1/42* (2006.01)
*C12N 13/00* (2006.01)
*B23K 26/384* (2014.01)
*C12N 5/00* (2006.01)

(52) U.S. Cl.
CPC ............ *C12N 15/87* (2013.01); *B23K 26/048* (2013.01); *B23K 26/0624* (2015.10); *B23K 26/0648* (2013.01); *C12M 35/02* (2013.01); *C12N 13/00* (2013.01); *B23K 26/384* (2015.10); *C12N 5/0006* (2013.01)

(58) Field of Classification Search
None
See application file for complete search history.

(56) References Cited

FOREIGN PATENT DOCUMENTS

WO    2011124899 A1    10/2011

OTHER PUBLICATIONS

Antkowiak, M. et al. "Application of Dynamic Diffractive Optics for Enhanced Femtosecond Laser Based Cell Transfection" (2010) J. Biophotonics 3 (10-11): 696-705.
Antkowiak, M. et al. "Towards High-throughput Automated Targeted Femtosecond Laser Based Transfection of Adherent Cells" (2011) Frontiers in Ultrafast Optics: Biomedical, Scientific, and Industrial Applications XI. Eds. Neev, J. and Nolte S. Proc. of SPIE 7925 (1): 1-7.
Antkowiak, M. et al. "Femtosecond Optical Transfection of Individual Mammalian Cells" (2013) Nature Protocols 8 (6): 1216-1233.
McDougall, C. et al. "Targeted Optical Injection of Gold Nanoparticles into Single Mammalian Cells" (2009) Journal of Biophoton. 2 (12): 736-743.
Meacham, J.M. et al. "Physical Methods for Intracellular Delivery: Practical Aspects from Laboratory Use to Industrial-scale Processing" (2014) Journal of Laboratory Automation 19 (1): 1-18.
Stevenson, D.J. et al. "Single Cell Optical Transfection" (2010) J.R. Soc. Interface 7: 863-871.
Tsampoula, X. et al. "Femtosecond Cellular Transfection Using a Nondiffracting Light Beam" (2007) Applied Physics Letters 91 (5): 53902-53902.
Waleed, M. et al. "Single-cell Optoporation and Transfectino Using Femtosecond Laser and Optical Tweezers" (2013) Biomedical Optics Express 4 (9): 1533-1547.

*Primary Examiner* — Robert M Kelly
(74) *Attorney, Agent, or Firm* — Volpe and Koenig, P.C.

(57) ABSTRACT

A method for the optoinjection of exogenous material in a recipient biological cell is disclosed and comprises: placing a biological cell on a planar surface of a substrate, transmitting a sub-ns pulsed laser beam through a variable convergence/divergence collimator; focusing the laser beam in a focal spot positioned along an axial direction substantially perpendicular to the substrate; moving the focal spot towards the cell along the axial direction by continuously varying the electric control signal from a first amplitude value a second amplitude value the second amplitude value of the control signal is selected such that the second axial position is positioned inside the cell.

11 Claims, 6 Drawing Sheets

METHOD FOR THE OPTOINJECTION OF EXOGENOUS MATERIAL INTO A BIOLOGICAL CELL

CROSS REFERENCE TO RELATED APPLICATIONS

This application is a 35 USC § 371 national stage application of PCT/IB2016/057829, which was filed Dec. 20, 2016 and claimed priority to IT 102015000088892, filed Dec. 30, 2015, both of which are incorporated herein by reference as if fully set forth.

FIELD OF THE INVENTION

The present invention relates to a method for the optoinjection of exogenous material into a biological cell.

BACKGROUND OF THE INVENTION

The introduction of exogenous genetic material (transgene) or foreign molecules in living cells has been found, during the last decades, to be a powerful tool in modern molecular biology. In the case of incorporation of exogenous DNA molecules in eukaryotic cells, usually mammals, it is called transfection, which may be transient or stable. More generally, the interest is for the incorporation of different materials foreign to the cell, such as imaging agents, peptides, antibodies, enzymes or pharmacologically active molecules.

Several techniques have been developed to introduce exogenous material in the cytoplasm or in the nucleus of a eukaryotic cell, among these chemical methods, viral methods and physical methods. The eukaryotic cell is enclosed in a cell (or plasma) membrane that delimits it and has a typical thickness of about 5 nm. The introduction of exogenous material through physical methods takes place by the passage through the cell membrane.

Physical methods often used are electroporation and microinjection. In electroporation, the cells are immersed into a solution containing the DNA or the molecules to be introduced and are subjected to short and intense electric pulses that produce transient pores in the cell membrane through which the exogenous material can enter. Microinjection consists in introducing the material directly into the nucleus or in the cytoplasm of the cell using a thin needle attached to a microinjector.

Effective insertion techniques that can be used on the vast majority of cell types use a laser beam to create a localized transient membrane rupture. In particular, in optoinjection (or optical injection), high-intensity laser pulses generate transient pores in the membrane which allow the influx of extracellular material within the cell.

An overview of the physical methods is given by Meacham J. M. et al. in "*Physical methods for intracellular delivery: practical aspects from laboratory use to industrial-scale processing*" published in Journal of Laboratory Automation, vol. 19 (2014), pages 1-18.

The cell membrane is a thin layer of hydrophobic lipids soaked in protein molecules which cross the membrane or are positioned on the inner or outer surface thereof. The cell's lipid nature makes sure that, under normal conditions, the membrane acts as a waterproof barrier to the passage of most water-soluble molecules. In techniques that use the interaction of a laser beam with the cell, obtaining an accurate alignment and positioning of the laser beam focus on the thin membrane is often a difficult and time-consuming task.

There are several known mechanisms that enable the transient perforation of cells, including methods that take advantage of a two-photon process using a femtosecond laser as the optical source. In "*Femtosecond cellular transfection using a nondiffracting light beam*" by X. Tsampoula et al., published in Applied Physics Letters 91, 053902 (2007), the authors use a Bessel beam to obviate the need to precisely locate the laser focus on the cell membrane, allowing the two-photon excitation along a line leading to the cell transfection.

Stevenson D. et al. in "*Femtosecond optical transfection of cells: viability and efficiency*", Optics Express, vol. 14, no. 16, page 7125, present a femtosecond optical transfection efficiency analysis using an 800 nm titanium sapphire laser.

A method of optical injection uses a nano- or microparticle optically trapped on the surface of a cell to be injected into the cell. In "*Targeted optical injection of gold nanoparticles into single mammalian cells*", C. McDougall et al., in J. Biophotonics 2, 736-743 (2009), the authors study an optical technique for inserting a nanoparticle of gold of 100 nm in diameter within a single cell by combining optical trapping and optical injection. The described optical apparatus includes a femtosecond laser for optical injection and a continuous wave laser for optical trapping. The positioning of the laser beam focus was obtained through an xyz translation system on which the sample dish was placed. According to the authors, the pulsed source causes a transient optical force on a nanoparticle and this has been believed to promote the entry of the nanoparticle through the cell membrane.

Patent application WO 2011/124899 relates to a method for poration of the membrane of biological cells in a specific area and the large scale poration with microbubbles excited by the rupture induced by laser light of single optically trapped nanoparticles.

Waleed et al. in "*Single-cell opto-poration and transfection using femtosecond laser and optical tweezers*", Biomedical Optics Express Vol. 4, No. 9 (2013), describe a transfection technique which involves trapping and inserting a plasmid-coated polystyrene microparticle in an MCF-7 cell. The cell membrane is first pierced and then the microparticle is inserted into the cell using optical tweezers. Three laser beams are used: the first beam is a femtosecond laser at 800 nm to pierce the membrane; the second is a continuous wave (CW) laser at 1064 nm, whose function is to trap and insert the microparticle in the cell, while the third laser beam is a CW laser at 685 nm, which senses the exact position of the membrane so that the 1064 nm entrapping laser can introduce the microparticle through the pierced hole in the cell membrane.

Antkowiak et al. in "*Application of dynamic diffractive optics for enhanced femtosecond laser based cell transfection*", J. Biophotonics 3, No. 10-11, 696-705 (2010), describes the use of a spatial light modulator (SLM) which acts as a dynamic diffractive optical element, which provides a lateral and axial beam control. The authors studied the feasibility of applying radiative doses at various axial and lateral positions using the SLM. In one method, the beam is focused sequentially in three different axial positions separated by 1 µm with a 700 ms delay between consecutive doses, which the authors say is a delay long enough to avoid any accumulation process of the photon energy. The authors conclude that the radiation in three axial positions doubles the number of cells actually optoinjected compared to a single dose.

SUMMARY OF THE INVENTION

The present disclosure describes a method and an apparatus for the optoinjection of exogenous material in a single biological cell that uses a sub-ns pulsed laser beam.

Eukaryotic cells typically have a maximum thickness of between 10 μm and 20 μm. The membrane enclosing the cell has a thickness of about 5-8 nm, which is significantly less than the size of the focus region, hereinafter referred to as focal spot, of the sub-ns laser beam often used for the optical piercing of the membrane.

The Applicant noted that an accurate positioning of the focal spot of a laser beam on the cell membrane is often complex and in most cases requires a laborious alignment of the laser beam. An incorrect positioning of the focal spot on the membrane can lead to having a relatively large percentage of failure of injection of extracellular material or irreversible damage to the transfected cell.

The Applicant also noted that, although using a Bessel beam can simplify the focusing of the laser beam on the cell membrane, the membrane perforation using Bessel beams may require a relatively high optical power to obtain a sufficient energy fluence in the central region of the beam. Such a power could produce undesired thermal effects in some types of cells.

The exogenous materials to be transfected or in general, to be introduced within a living biological cell is typically contained in a liquid solution in contact with the outer surface of the cell, in the description below also referred to as extracellular solution. In many cases of interest, the recipient biological cell is immersed in the extracellular solution. The Applicant has understood that a continuous displacement of the focal spot of the laser beam through a solution containing exogenous material towards the recipient cell allows an efficient injection of exogenous material flow into the cell. In particular, the Applicant has understood that since a focused laser beam having relatively high optical power generates a very localized optical tweezers effect that attracts the molecules of the fluid, a continuous laser displacement generates a stream of extracellular solution optically directed towards the cell, thereby increasing the optical injection efficiency.

The Applicant has also understood that an electronic control of the axial displacement of the focused optical beam towards the cell has several advantages, among which allowing the beam to be kept on only during the descent of the focal spot towards the cell and switching the beam off when it is in an axial position within the cell, thereby reducing the photodamage induced by the optical beam into the cell.

The optoinjection method can be carried out without the need of an axial positioning of the focal spot on the cell membrane to ensure the (transient) perforation of the membrane itself and thus to allow the optoinjection.

According to the present disclosure, a continuous axial displacement of the focal spot is implemented using a variable convergence/divergence collimator. The variable convergence/divergence collimator is optically coupled with a sub-nanosecond pulsed laser source and comprises a lens with tunable focal length whose change in the focal length controls the degree of convergence/divergence of the optical beam from the collimator.

In some preferred embodiments, the optoinjection process may be repeated at least a second time and in general a desired number of times by bringing the switched-off beam back to an axial position outside the cell and above it. Once the beam has been switched on again, the process involves continuously axially moving the focal spot in the direction of the cell until the beam penetrates into the cell itself. In this way, it is possible to increase the amount of injected exogenous material and automate the optoinjection process, thereby improving the efficiency thereof.

A method is described for the optoinjection of exogenous material into a recipient biological cell, wherein the cell comprises a cell membrane which encloses it, the method comprising:

placing a biological cell on a planar surface of a substrate, the cell having a basal surface resting on the planar surface of the substrate and an apical surface opposite the basal surface and in contact with a fluid solution which contains exogenous material;

transmitting a sub-ns pulsed laser beam through a variable convergence/divergence collimator, the collimator comprising a lens with focal length tunable by means of a variable amplitude control electrical signal;

directing the laser beam, having passed through the collimator, through an objective lens to focus the laser beam in a focal spot along an optical axis defining an axial direction substantially perpendicular to the planar surface of the substrate, such that the focal spot is positioned along the axial direction;

setting the electric control signal to a first amplitude value which defines a first focal length of the lens, corresponding to a first axial position $z_i$ of the focal spot along the optical axis, wherein the first amplitude value of the control signal is selected such that the first axial position $z_i$ is above the apical surface of the cell at a first axial distance from the planar surface of the substrate, and moving the focal spot towards the cell along the axial direction by continuously varying the control electric signal from the first amplitude value to a second amplitude value, the second amplitude value defining a second focal length corresponding to a second axial position $z_f$ of the focal spot, wherein the second amplitude value of the control signal is selected such that the second axial position is positioned inside the cell, at a second axial distance from the planar surface of the substrate, less than the first axial distance, such that the focal spot traverses the membrane of the cell during the descent of the focal spot towards the cell producing a pore in the membrane, which allows the fluid solution containing exogenous material to enter the cell.

The method according to the present disclosure allows the optoinjection of a single cell with sub-cellular accuracy.

In some embodiments, the control signal is a voltage electrical signal and the first amplitude value is a first voltage value and the second amplitude value is a second voltage value.

In this context and according to some embodiments, with "substantially perpendicular" with reference to the optical axis of the focused laser beam it is meant that the optical axis may be at an angle less than or equal to 15°, preferably within 10°, with respect to the perpendicular.

In some embodiments, the method comprises, prior to the step of moving the focal spot towards the cell, laterally positioning the biological cell in the plane of the substrate surface so that an area of the recipient biological cell intercepts the focused optical beam along the axial direction.

Preferably, the objective lens is a microscope objective lens. Preferably, the beam exiting the variable convergence/divergence collimator is directed towards the input pupil of the objective lens and the beam exiting the lens is a focused beam along the optical axis of the lens.

In some embodiments, the travel axial distance of the focal spot of the laser beam is equal to $\Delta z=(z_f-z_i)$ and is comprised between 20 μm and 100 μm.

In some preferred embodiments, the control signal of the lens with tunable focal length is a frequency-modulated analog electric signal modulated at a frequency $f_{TL}$ that determines the speed of axial displacement of the focal spot, $v_{fs}$, during its descent from the first axial position to the second axial position, according to the relationship $v_{fs}=2\cdot(z_f-z_i)\cdot f_{TL}$.

Preferably, the speed of axial displacement of the focal spot is of from 10 μm/s to 500 μm/s, more preferably of from 80 to 150 μm/s.

Preferably, the variable convergence/divergence collimator further comprises a second converging lens of fixed focal length, the second lens being arranged with respect to the tunable focal length lens such that the laser beam traverses the second lens and the tunable focal length lens.

Preferably, the first axial distance from the planar surface of the substrate is selected taking account the maximum thickness of the recipient biological cell. In some embodiments, the first axial distance is selected in such a way as to have an axial distance from the cell of at least 10 μm with respect to the apical surface of the cell at the point of maximum height of the same.

In some embodiments, the second axial distance from the planar surface of the substrate is greater than zero and smaller than the minimum height of the recipient cell.

Preferably, the substrate constitutes the base of a container in which the recipient cell is arranged and in which the extracellular solution containing exogenous material is contained, the cell being immersed in the solution.

Preferably, the laser beam is a femtosecond pulsed beam.

Preferably, the laser beam is a Gaussian beam.

Preferably, before the step of transmitting a sub-ns pulsed laser beam through a variable convergence/divergence collimator, the method comprises emitting a sub-ns pulsed laser beam from a sub-ns pulsed laser source, wherein the variable convergence/divergence collimator is optically coupled to the laser source. In some embodiments, after the step of moving the focal spot with continuous displacement up to the axial position $z_f$, the method comprises switching off the laser source when the second axial position $z_f$ of the focal spot is reached.

In the present description and claims, exogenous material indicates one or more cell materials foreign to the cell, such as for example nucleic acids, imaging agents, peptides, antibodies, enzymes or pharmacologically active molecules. With optoinjection it is meant the injection of exogenous material assisted by a laser beam into a cell, this term including the injection of nucleic acids or DNA, namely the transfection.

If samples are in vivo, the cell or cells are usually cultured, distributed on the surface of a Petri dish and immersed in a culture medium, i.e. a liquid solution. Alternatively, cells cultured in vitro can be inserted in a multiwell plate. More generally, the cells may be contained in a receptacle, typically of glass or disposable plastic, containing the solution. In the sample imaging by means of fluorescence or bright field microscopy, the receptacles are usually made of transparent material, although in an upright microscope with epi-fluorescence illumination, receptacles of material not transparent to light may be used.

Imaging techniques, in particular investigative techniques on mammary cells, are often conducted on in vivo cells that are adhered (as a monolayer) to a substrate, which may be part of a container. For example, in a Petri dish, which is in substance a flat receptacle closable with a lid, the substrate on which the cells adhere constitutes the base of the plate.

BRIEF DESCRIPTION OF THE FIGURES

The present invention will hereinafter be described in greater detail with reference to the accompanying drawings, in which some embodiments of the invention are shown. The drawings illustrating the embodiments are schematic representations not in scale.

DETAILED DESCRIPTION

Figure 1:
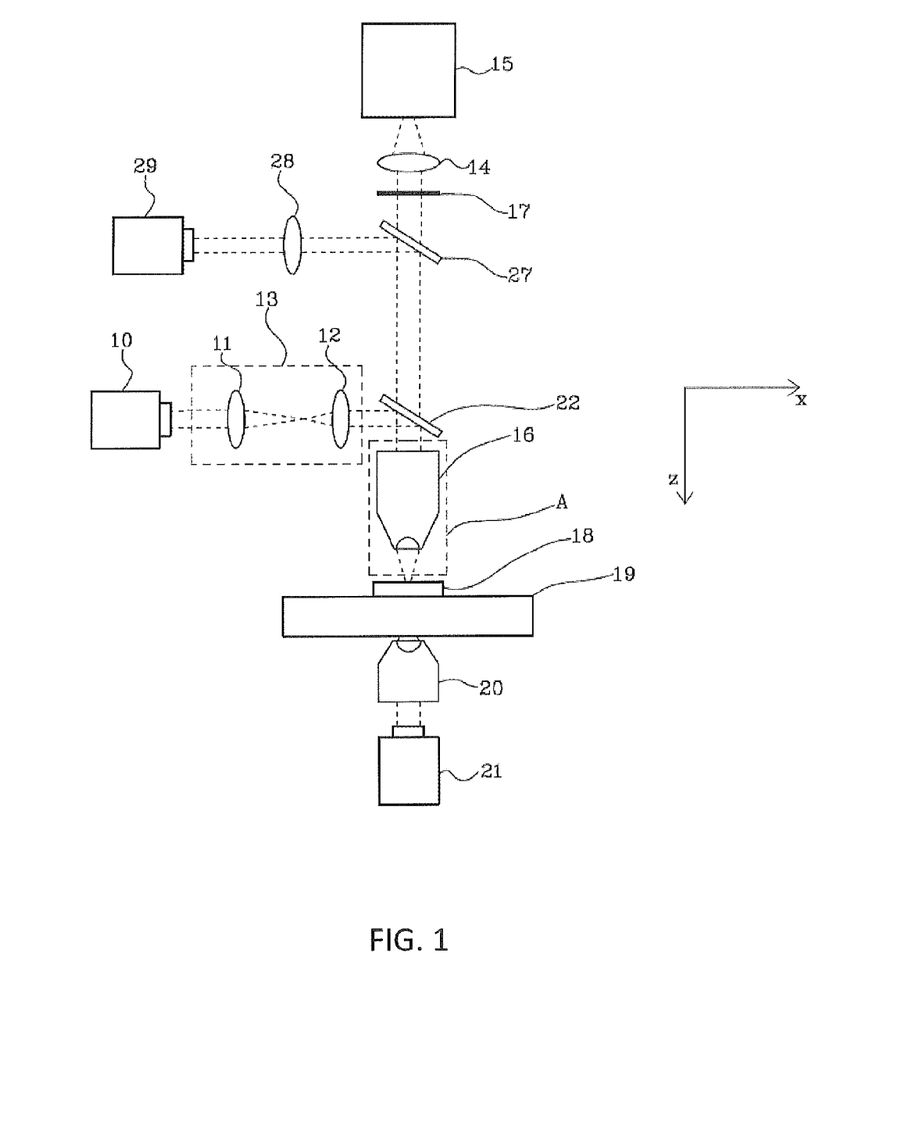
FIG. 1 is a schematic diagram of an apparatus for the optoinjection of a biological cell for the insertion of exogenous material into the cell, according to an embodiment of the present invention.

In FIG. 1, an optoinjection apparatus comprises a laser source 10 configured to emit a laser beam with ultrashort, sub-nanosecond pulses. The use of a pulsed laser source reduces the average optical power incident on the cell and thus the thermal effect in the cell. In general, with the same laser beam wavelength, the shorter the pulse duration, the lower the average power required to achieve the perforation of the cell. A pulse duration of less than a nanosecond is preferred in many embodiments since it prevents the creation of a shock wave during the ablation of the material. In some embodiments, the pulse duration is less than 500 picoseconds. Preferably, the laser source is a femtosecond pulsed laser. Preferably, the laser beam is Gaussian, i.e. has intensity profile of Gaussian shape.

The laser source is optically coupled to a variable convergence/divergence collimator 13 which comprises a lens of tunable focal length. The degree of convergence/divergence of the collimator varies according to the variation of the focal length of the lens. In the preferred embodiments, the focal length is electrically tunable via an electrical control signal.

In the embodiment shown in FIG. 1, collimator 13 comprises a first lens 11 with fixed focal length and a second lens 12 with tunable focal length, arranged downstream of the first lens 11 with respect to the laser source 10. The lens with tunable focal length will be hereinafter referred to, for the sake of brevity, also to as tunable lens. In the embodiment shown in FIG. 1, the first lens 11 is a converging lens, for example a convex lens, and the second lens 12 with tunable focal length is a converging lens, for example a convex lens.

In another embodiment (not shown in the figures), collimator 13 comprises a converging lens with tunable focal length that receives the laser beam emitted by the laser source and a converging lens with fixed focal length, arranged downstream of the tunable lens.

The laser beam, after passing through collimator 13 and in particular the tunable lens 12, impinges on a first optical deflection element 22 that deflects the laser beam by directing it toward the input pupil of a microscope objective lens 16. The laser beam is focused by the objective lens 16 forming a focused beam in a spot of finite size.

For example, the focal spot of a sub-ns pulsed laser beam which emits radiation at 355 nm may have a size of about 500 nm along the optical axis. Again by way of example, with a pulsed infrared laser, which emits light at a wavelength of about 1000 nm, a size of the focal spot of about 1600 nm may be obtained along the optical axis of the beam. The size of the focal spot depends, in addition to the wavelength of the laser beam, on the numerical aperture of the objective lens used. In general, the larger the numerical aperture, the smaller the size of the focal spot along the optical axis of the beam. A relatively small size of the focal spot typically implies a reduction of the optical power of the beam necessary to create an ablation phenomenon in the focus and thus a smaller photo-damage to the recipient cell.

The first optical deflection element 22 is preferably a planar mirror configured to reflect the laser beam coming from the collimator directing it towards the objective lens.

The optical axis of the microscope objective lens defines the axial incidence direction of the laser beam on the sample and is indicated in the figure as axis z, i.e. the optical axis of the incident beam. A focus adjustment along the optical axis of the beam exiting the objective lens is obtained by changing the divergence or convergence of the laser beam entering the objective lens by means of the variable convergence/divergence collimator. In particular, the variation of the focal length of the tunable lens in combination with the focusing of the beam produced by the objective lens results in a variation in the axial position, i.e. along the z optical axis, of the focal spot.

Figure 1A:
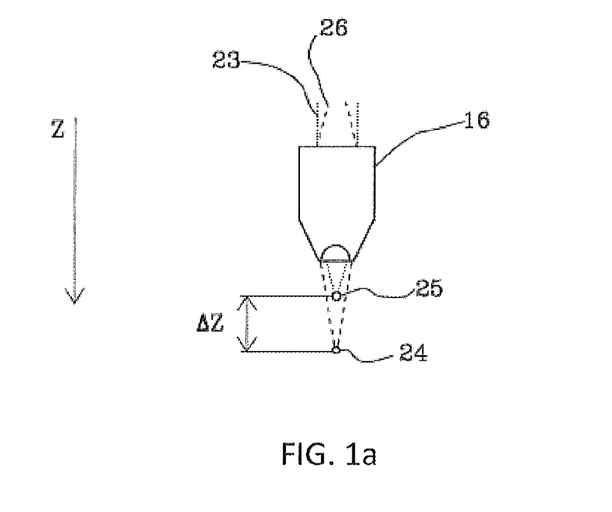
FIG. 1a is an enlargement of a portion of FIG. 1 indicated with a dash-dot box A, in which, by way example, the focal spots corresponding to two different focal lengths of the tunable lens are compared.

A partial enlargement of FIG. 1, indicated with a dash-dot box A in FIG. 1, is shown in FIG. 1a, in which, by way example, the focal spots corresponding to two different focal lengths of the tunable lens 12 are compared. The first laser beam 23 (dotted line) that enters the objective lens 16 is constructed with a first focal length $l_1$ of the tunable lens, while the second beam 26 (dashed line) relates to a second focal length $l_2$ of the tunable lens. In output from the objective lens, the first laser beam is collimated in a focal spot 25 positioned in a first axial position, while the focal spot 24 of the second laser beam is positioned in a second axial position which is $\Delta z$ away from the first axial position.

With reference again to FIG. 1, in a plane transverse to the optical axis of the objective lens and therefore of the direction of incidence of the laser beam a sample holder 18 is arranged, preferably a container containing a biological sample, and in particular one or more cells to be optoinjected or in particular to be transfected. In the present context, a "target" cell to be optoinjected with exogenous material is referred to as recipient cell.

Preferably, the focal length of the second lens 12 is electrically controllable by means of an (electric, mechanical or electromagnetic) actuator connected to a current or voltage regulator that provides current/voltage from zero to a maximum value. In the usual ways, the current or voltage supplied to the actuator can be controlled electronically by a software, for example integrated in the electronic control system of the optoinjection apparatus. Although not shown in FIG. 1, the tunable lens comprises an actuator that controls the focal length of lens 12, in which the actuator is connected to a current or voltage regulator, in turn connected to an electronic control unit (also not shown in the figure).

An electronic control of the focal length of the tunable focal length lens, and thus of the axial position of the focal spot has, in many embodiments, the advantage of achieving a relatively fast axial displacement, with controlled displacement speed, as described more in detail hereinafter.

In one embodiment, the tunable lens is a shape-changing liquid lens formed by an elastic polymeric membrane that encloses an optical fluid. An electromagnetic or mechanical actuator is integrated on the lens, which controls a ring that is positioned on the surface of the polymeric membrane and that induces a variation of the pressure exerted on the liquid of the lens, thereby changing the curvature of the lens. In this way, the voltage regulator controls the actuator by controlling the deflection of light passing through the lens and the focus position therewith.

The size of the focal spot in general depends on the wavelength of the laser beam and on the numerical aperture of the objective lens used. In some embodiments, the focal spot of the laser beam has a diameter of between 200 nm and 300 nm in the plane (x, y) perpendicular to the optical axis z and a diameter of between 300 nm and 1000 nm along the optical axis.

Since in many embodiments it may be advantageous to detect the flow of the extracellular solution inside the recipient cell, the optoinjection apparatus comprises an optical imaging system (e.g. fluorescence or bright field) caused by the injection of the solution into the cell. The imaging system may be a per se known system used in optical bright field or fluorescence microscopes.

In the embodiment in FIG. 1, the optical imaging system allows both bright field microscopy and fluorescence microscopy. Preferably, the first optical deflection element 22 is a dichroic mirror configured in such a way as to reflect the wavelength of the laser beam wave to induce a laser ablation on the cell, and at the same time let the emission light from the sample pass through. In bright field imaging, the imaging technique is in transmitted light and the apparatus comprises a first illumination source 21, for example a halogen lamp, arranged so as to illuminate from below the biological sample in a sample area that intercepts the laser beam. The light of source 21, preferably broad-spectrum, is focused on the sample through a condenser 20. The dichroic mirror 22 is configured in such a way as to let the light emitted by the halogen lamp and transmitted through the sample pass through. The optical features of the dichroic mirror are selected according to the wavelength of the pulsed laser beam and of the fluorescence or emission optical spectrum of the exogenous molecules.

If the imaging technique is fluorescence (in FIG. 1, in epi-illumination configuration), the apparatus comprises a second illumination source 29, preferably a xenon lamp, which emits light focused by a convex lens 28, and a second optical deflection element 27, preferably a dichroic mirror which reflects the excitation light from the xenon lamp and which lets the fluorescence light emitted by the sample pass through.

The fluorescent light emitted by the sample is collected by the microscope objective lens 16 that directs it towards the dichroic mirror 22, which is configured so as to transmit the beam scattered by the sample and reflect the collimated beam coming from the laser source. The light transmitted by the dichroic mirror 22 is directed toward a photodetector device 15, which preferably comprises a CMOS camera or a CCD camera.

In the use of the optoinjection apparatus in bright field microscopy, the xenon lamp 29 remains off while the halogen lamp 21 is on. The light emitted by the halogen lamp 21 passes through the sample and is collected by the objective lens 16 that directs it towards the dichroic mirror 22 and the dichroic mirror 27, which let a portion of light emitted by the halogen lamp pass, which is detected by the detection device 15.

Preferably, if using fluorescence imaging, the apparatus comprises a fluorescence filter 17 arranged along the detection direction, in FIG. 1 along axis z, and arranged in such a way as to interfere with the light coming from the sample and collected by the microscope objective lens 16. As per se generally known, the fluorescence filter blocks the excitation light and allows the fluorescent light to pass through by exploiting the fact that the fluorescent light is usually emitted at a longer wavelength than the excitation light.

Preferably, the detection system also comprises a tube lens 14 arranged along the detection direction between the objective lens and the photodetector device 15. As per se generally known, the tube lens is configured to focus the parallel light beam (i.e. subjected to infinite imaging) outgoing from the objective lens at an intermediate image plane. Then, the focused fluorescent or illumination light is detected by the photodetector device 15.

Preferably, the objective lens 16 has a large numerical aperture (NA), since a greater numerical aperture generally implies a greater focusing of the laser beam (i.e. smaller focal spot) and a more efficient ablation of the sample, making it unnecessary to use relatively high beam intensities such as to induce the heating of the cell, and thereby photo-damage. In some embodiments, the objective lens has a numerical aperture of between 0.4 and 1.49.

The sample holder 18 comprises a substrate arranged in the plane (x, y) perpendicular to the optical axis z of the objective lens 16, and thus to the direction of incidence of the beam. Preferably, the sample holder 18 is arranged on a translation system 19 along the axes (x, y, z) for the lateral positioning of the cell with respect to the incident beam, and for focusing the cell in the optical microscope.

In some embodiments, the optoinjection apparatus comprises an upright microscope (as in FIG. 1) in epi-illumination fluorescence, which allows the visualization of cells also on non-transparent supports, such as a matrix of non-transparent micro-electrodes of the type typically used to measure the electrophysiological activity of the cells. However, the method according to the present disclosure may also be applied on an inverted microscope, which usually uses an oil objective lens with NA of 1 to 1.5. If the apparatus in FIG. 1 is used with the bright field imaging technique, support 18 is transparent so as to allow the transmission of the light emitted by the first illumination source 21 through the biological sample.

The optical microscope is used to visualize the cells and place a desired portion of the recipient cell in such a way that it intercepts the optical axis of the laser beam. In the usual manners, the translation system 19 has a window made of a light transparent material to allow the illumination of the sample portion to be visualized.

The method according to the present disclosure may use a fluorescence microscope, for example in the case in which molecules introduced into the cell emit photoluminescence when irradiated. In this case, elements 20 and 21 for the back-lighting of the sample are not required.

Without limitation to the solution described herein, the following description of some embodiments will refer to a solution which contains exogenous molecules to be inserted into a single cell in vivo, whose membrane is not permeable to said molecules.

Figure 2:
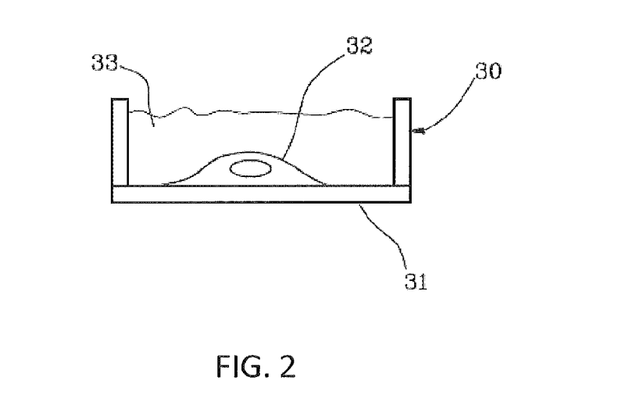
FIG. 2 is a schematic representation of a sample holder in which the biological cell to be injected with exogenous material is positioned, according to an example.

Preferably, the biological cell is arranged on a substrate arranged in a plane (x, y) perpendicular to the optical axis z, and arranged in such a way that a desired region of the cell intercepts the laser beam. FIG. 2 is a schematic representation of a sample holder in which the biological cell to be injected with exogenous material is positioned, according to an embodiment example. The sample holder is a receptacle 30, for example a Petri dish, which comprises a base 31 on which a biological cell 32 adheres. Base 31 constitutes the substrate on which the cell is positioned and is preferably made of optically transparent material. The biological cell 32 is in contact with a liquid extracellular solution 33 which covers it and which contains a plurality of molecules to be introduced into the cell. If the cell membrane is not permeable to said molecules, the insertion of the same requires the piercing of the membrane itself.

A high intensity pulsed laser beam focused through an objective lens can create a transient pore through the cell membrane, thus resulting in an osmotic influx of extracellular (exogenous) molecules within the cell. The optical power required to pierce the membrane generally depends on the laser source employed, and in particular on the laser beam wavelength and on the duration of the pulses. In some embodiments, the laser beam has an optical power of between 10 µW and 200 mW and a wavelength of between 350 nm (ultraviolet) and 900 nm (infrared).

The lateral dimension of the pore depends, among other factors, on the size of the piercing focal spot. In general, in the case of eukaryotic cells with focal spots of lateral size of 100-200 nm in the plane (x, y) parallel to the substrate, the pore has a size greater than a single molecule and the technique therefore allows the opto injection of a plurality of molecules with a single membrane piercing.

In the analysis of living cells, the cells are adhered to a substrate and immersed in the extracellular solution so that there is a liquid layer on the apical surface of the cell. By way of example, the thickness of the liquid layer that covers the cell may typically vary approximately between 1 mm and a few millimeters, depending also on the sample holder container used.

According to the present disclosure, the focal spot of the beam moves axially in a continuous manner from an initial axial position, $z_i$, towards the cell, passing through the extracellular solution up to a final axial position $z_f$ inside the cell, along an axial distance equal to $\Delta z = (z_f - z_i)$.

Preferably, the initial axial position $z_i$ is above the cell, at an axial distance from the surface thereof. Preferably, the initial axial position, $z_i$, is internal to the extracellular solution that covers the cell and the focal spot passes through a thickness of the liquid layer of solution above the cell up to a position $z_f$ inside the cell.

The optical axis of the incident beam along which the axial displacement of the focal spot occurs is generally transverse to the planar surface of the substrate on which the recipient cell is arranged. In general, the angle formed between an axis perpendicular to the planar surface of the substrate and the optical axis of the beam cannot be greater than the maximum angle, $\alpha_{max}$, dictated by the numerical aperture of the objective lens: $\alpha_{max} < \arcsin(NA/n)$, with n being the refractive index of the immersion medium of the objective lens. The Applicant has observed that the more the optical axis of the incident beam is inclined with respect to the perpendicular, the greater the necessary excursion of the focal spot to reach the position $z_f$ starting from the initial position $z_i$, the axial positions being defined with respect to an optical axis perpendicular to the planar surface of the substrate.

In the embodiments according to the present disclosure, the axial direction of the optical beam in output from the objective lens along which the axial displacement occurs is substantially perpendicular to the substrate. In a preferred embodiment, the optical axis of the objective lens and therefore the axial direction of the incident laser beam is perpendicular to the planar surface of the substrate.

Once reached the final position, it is preferable to switch off the beam to avoid generating an optically induced flow of liquid that goes in the opposite direction (from the cell towards the solution) to that created during the descent of the laser beam (towards the cell). Moreover, in some applications of interest, returning the position of the focal spot to $z_i$ with beam off reduces the risk of inducing a thermal damage in the cell structure.

Figure 3:
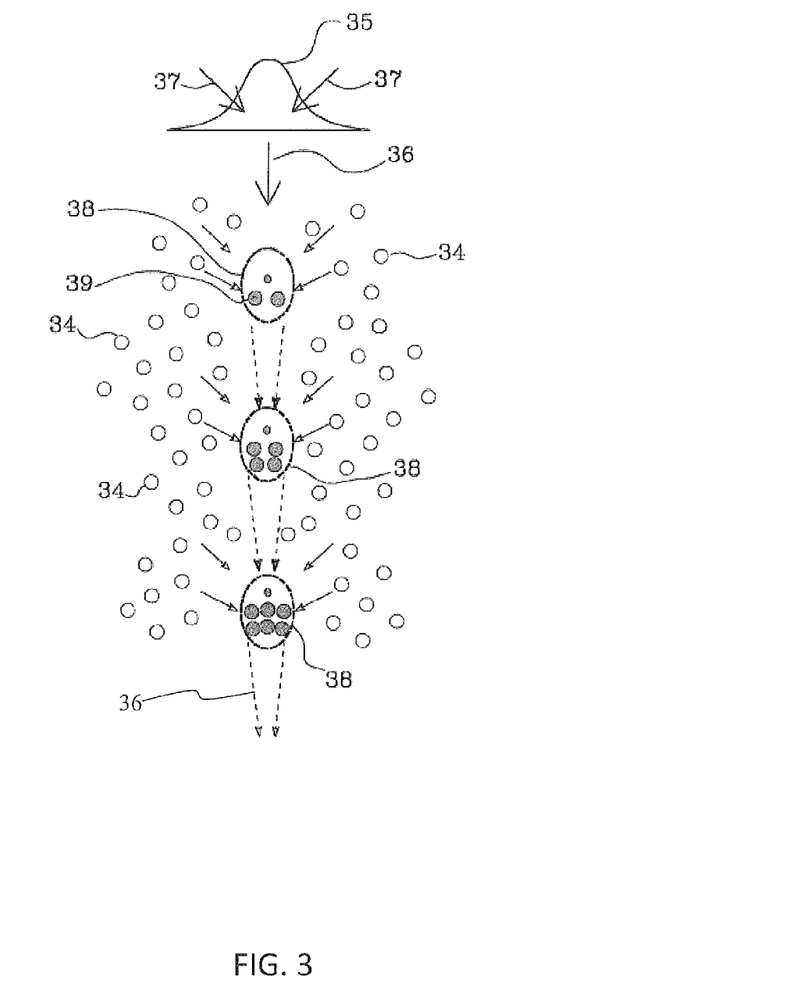
FIG. 3 schematically shows the flow of exogenous molecules optically generated by the focal spot during the penetration of the same through the extracellular solution containing the exogenous molecules.

Without wishing to be limited to a particular theory or explanation, FIG. 3 schematically shows the flow of exogenous molecules optically generated by the focal spot when during the passage of the same through the extracellular solution containing the exogenous molecules, such as nucleic acid molecules, which are shown in the figure with circles 34. The laser beam intensity indicated with reference numeral 35 has a Gaussian distribution around the center of the focal spot. Such a distribution of optical intensity generates a gradient force, $F_{grad}$, which attracts the molecules towards the center of the spot, as schematically shown by arrows 37. The movement of the focal spot is from the top downwards. The center of the focal spot is shown in the figure with a dashed perimeter ellipse 38 (the shape is meant to be just a graphic representation without geometric meaning). Once the molecule reaches the center of the spot, it is pushed forward by the reflection power, $F_{scat}$ along the axial direction as shown by arrows 36, towards the cell. The molecules which enter into the focal spot, indicated with grey circles 39, feel the gradient and reflection optical forces and undergo an optically induced axial displacement. The optical forces created in the focal spot combined with a continuous axial movement attract increasingly more molecules from the surrounding fluid towards the focal spot of the laser and within the focal spot during the descent, due to the gradient force. The laser beam passing through the cell membrane creates a transient pore which allows the entry of molecules into the cell, for example, in the cytoplasm or nucleus.

Without wishing to bind the present disclosure to a particular theory or explanation, the Applicant believes that the optoinjection efficiency is relatively high, due to the synergistic action between creating a transient pore in the cell membrane to insert an osmotic flow of extracellular solution and the presence of an optically generated flow directed towards the membrane pore.

The Applicant has understood that by establishing an axial distance traversed by the focal spot, a placement on the cell membrane is not required to create a pore in the same. The axial distance traversed by the focal spot along the optical axis of the laser beam, $\Delta z$, is defined between a starting position, $z_i$, at which the laser beam is switched on, and a final position, $z_f$, at which the laser beam is switched off, $\Delta z = (z_f - z_i)$. The final position is selected so as to be located within the cell, i.e. beyond the axial position of the membrane in the cell area impinged by the laser beam.

Each axial position of the focal spot corresponds to a focal length of the tunable lens optically coupled to the laser beam coming from the laser source. For an electrically tunable lens, each focal length value in turn corresponds to an electric voltage or current value applied to the electrodes of the lens. More generally, each electric control signal amplitude value of the tunable lens corresponds to a focal length value.

If the electrical signal is analog, a control unit controls the tunable lens driver so as to vary the amplitude of the signal (voltage or current) from a first amplitude value to a second amplitude value in infinitesimal increments (or decreases) in order to have a continuous variation (i.e. not discretized) of the focal length of the lens.

In some embodiments, the control signal of the tunable lens is a periodical electric signal, not square-wave, to continuously and gradually change the position of the laser focus on the sample from $z_i$ to $z_f$ and vice versa, and thus prevent step changes between the two selected positions $z_i$ and $z_f$, which induce ripple phenomena on the control signal prior to the stabilization of the control signal to a new value.

The tunable lens associated with a signal amplitude regulator for the control thereof may be a commercial device, typically available with control software to be installed in the electronic control unit of an experimental apparatus.

Figure 4:
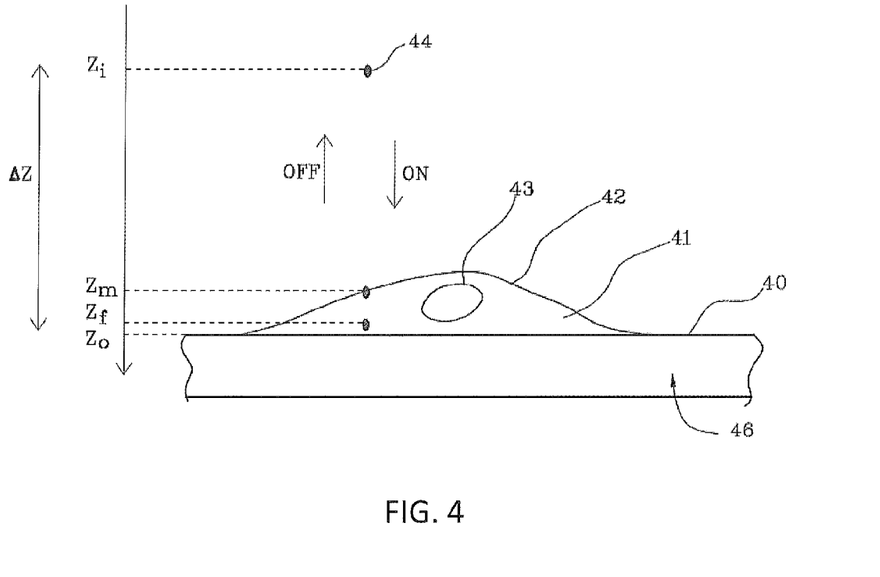
FIG. 4 is a schematic graphic representation of an optoinjection procedure according to an embodiment.

FIG. 4 is a schematic graphic representation of an optoinjection procedure according to an embodiment. In many experimental situations, both in vivo and not in vivo, the recipient cell is resting on, and in particular adhered to, a planar surface of a substrate. The "height" of the cell may be defined by the distance between the apical surface and the basal area, the latter resting on the substrate surface. Since height is a variable along the free cell surface, the maximum height of the cell is usually indicated. In the figure, a eukaryotic cell 41, of which nucleus 43 is indicated, is arranged on a planar surface 40 of a substrate 46. The cell is enclosed by a membrane 42 that defines the outer surface thereof. The cell is immersed in a fluid solution containing exogenous material, not shown in the figure for better clarity. Being resting on the substrate surface, the lower surface of the cell may be considered to correspond to the upper surface 40 of substrate 46, thus defining an axial reference position $z_0$, along axis z.

At the starting axial position $z_i$ the beam is switched on, indicated by the focal spot 44. The starting axial position is established by an initial voltage value, $V_i$, of the electrical control signal of the tunable lens, selected in such a way that position $z_i$ is at an axial distance with respect to the apical surface of the cell.

Considering that the maximum height of a cell is about 20 μm, the starting axial position $z_i$ is selected so that it is at an axial distance from surface 40 of substrate 46 on which the cell lies. Preferably, the starting axial position $z_i$ is at an axial distance with respect to the apical surface of the cell of at least about 10 μm. Eukaryotic cells typically have a maximum thickness of 10-20 μm, generally not uniform when they are resting on a flat surface. For example, a neural cell plated on a Petri dish reaches a maximum height of about 10 µm. In this case, it is preferable to set a starting axial position to at least 40 µm with respect to the substrate. Preferably, the starting axial position is at an axial distance of between 50 µm and 30 µm, with respect to the substrate.

The final voltage value, $V_f$, related to the final axial position $z_f$, is selected such that the final position is inside the cell. In order to ensure the integrity of the cell, especially if in vivo, it is preferable that the focal spot does not completely cross the thickness of the cell, so as to prevent perforation of the membrane in the surface opposite to the direction of entry of the beam. With reference again to the example of a neuron, the minimum height of the cell between the apical surface and the basal surface is about 5 µm. In this example, the axial distance from the planar surface of the substrate for position $z_f$ is preferably selected at a value greater than zero and less than 5 µm. In one embodiment, the axial distance from the planar surface of the substrate is 3 µm.

Taking as reference the position $z_0$ corresponding to the planar surface of the substrate, the starting axial position may be expressed as $z_i=z_0+m_1$, where $m_1$, where m is a positive real number. The final position, $z_f$, at which the laser beam is switched off may be expressed with $z_f=z_0+m_2$, where $m_2$ is a positive real number less than $m_1$, $m_2=m_1-\Delta z$, with $\Delta z>0$.

In some embodiments, the position of point $z_0$ is determined and the values of the axial distances $m_1$ and $m_2$ are selected such that $m_1$ is greater than the maximum thickness of the cell and $m_2$ is smaller than the minimum thickness of the cell.

In one embodiment and by way of example, $m_1=25$ µm and $m_2=3$ µm, so as to have an axial displacement which covers the distance between $z_0+25$ µm and $z_0+3$ µm, i.e. $\Delta z=21$ µm.

In one embodiment, the value $z_0$ is determined in a calibration step which precedes the optoinjection step, in which the focal spot is moved from above through the liquid towards the surface of the substrate without biological sample. Therefore, when the laser focus reaches surface 40 of substrate 46, a small hole is formed on the surface, ablated by the laser focus itself. The formation of this hole is visible through the imaging system.

FIG. 4 also shows the axial position along the optical axis z of the beam at the cell membrane, $z_m$. According to the embodiments of the present description, it is not necessary to determine the position $z_m$, since it is between an established starting position at a certain height with respect to the apical surface of the cell and an established arrival position of the focal spot inside the cell.

In the preferred embodiments, when the laser beam reaches the position $z_f$, it is switched off so that during the removal of the beam from the cell along the axial direction, it does not create a fluid flow in the opposite direction which counteracts the flow generated previously directed towards the inside of the cell. Moreover, switching off the laser beam reduces photo-damage to the cell.

In some preferred embodiments, after switching off the beam at position $z_f$, the control signal of the tunable lens is set back to a signal amplitude value which corresponds to the starting axial position $z_i$. The focal spot of the beam is therefore positioned at a certain height with respect to the apical surface of the cell and the optoinjection operation is repeated a second time by driving, by means of the control unit, the descent of the focal spot to the axial position $z_f$ at which the beam is switched off. In general, the optoinjection procedure may be repeated a desired number of times.

The control signal amplitude variation and thus the change in focal length is configured in such a way as to achieve a continuous variation of the axial position of the focal spot. As is generally known, the continuity of signal variation depends on the control electronics which establishes the differential variation (increases or decreases) of width of the control signal of the tunable lens between an amplitude value and the next one. Preferably, the control signal of the tunable lens is an analog current signal, as it allows a continuous (not step) variation of its focal length.

However, the present description does not exclude the use of a digital control signal for the tunable lens. In the case of digital control signal, the size of the discrete variations of the focal length depends on the number of bits in the digital signal. For example, an 8-bit resolution A/D converter encodes an analog input control signal in $2^8=256$ discrete values. For example, if the tunable lens has 90 mm of focal length variation range, for example, from a minimum of 45 mm to a maximum of 135 mm, the minimum variation in the focal length is equal to 90/256, or 0.35 mm. Using A/D converters with higher resolution, such as greater than or equal to 12 bit, reduces the minimum possible variation in the focal length.

The Applicant has noted that the use of a frequency-modulated control signal of the tunable lens, in which the frequency is variable within a range of values, allows selecting the displacement speed of the focal spot along the optical axis of the beam. The displacement speed may be selected depending on the type of target cells and/or the material to be injected. The Applicant has noted that, especially in the case of cells in vivo, a relatively low speed involves a relatively long interaction time of the laser beam with the cell, and under some conditions the optoinjection operation may create photo-damage.

In some embodiments, the frequency of the electrical control signal is selected in such a way as to achieve an axial displacement speed of the focal spot of between 10 µm/s and 500 µm/s, preferably between 80 and 150 µm/s.

The focal spot axial displacement speed, $v_{fs}$, is a function of the control signal frequency of the tunable lens, $f_{TL}$, and/or of the axial distance $\Delta z=(z_f-z_i)$ traversed by the beam during its descent toward the cell:

$$v_{fs}=2\cdot(z_f-z_i)\cdot f_{TL}. \quad (1)$$

At a constant axial distance $\Delta z$, increasing the frequency involves an increase in the axial displacement speed.

The laser beam is pulsed, sub-ns. For a beam with constant pulse rate, a change in the axial displacement speed causes a change in the number of pulses per unit length, $N_{pulses}$/µm. Positions $z_i$ and $z_f$ are selected by varying the amplitude of the electric signal applied to the electrodes of the tunable lens:

$$N_{pulses}/\mu m=(\text{pulse frequency})/v_{fs} \quad (2)$$

In some preferred embodiments, the tunable lens is controlled by means of a voltage electrical signal of (maximum) amplitude $V_0$ modulated with frequency $f_{TL}$, for example $V(t)=V_0 \sin(2\pi f_{TL} t)$. The voltage value V(t) corresponds to a given focal length of the tunable lens and thus to a given focal position along the optical axis of the incident beam, while the frequency determines the axial displacement speed according to the Eq. (1) above.

Figure 5:
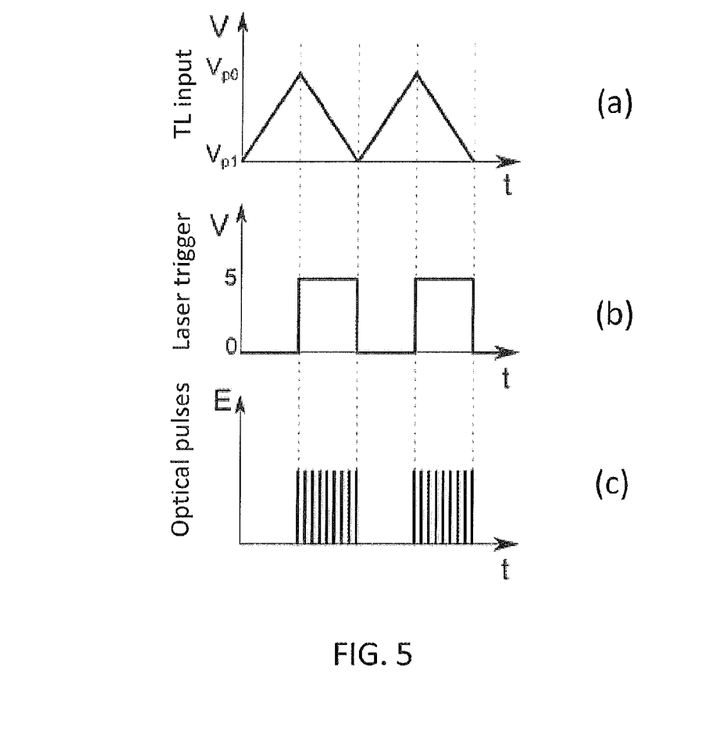
FIGS. 5a-5c show: an exemplary control signal of the tunable focal length lens (TL) (a), a trigger for switching on and off the laser beam (b) and a number of pulses during the switching on of the beam (c), according to an embodiment of the invention.

FIG. 5a shows a possible voltage control signal of the tunable focal length lens with triangular waveform which varies as a function of time, from a first value $Vp_0$ to a second value $V_{p1}$, thus axially moving the focal spot from the axial position $z_i$ to the axial position $z_f$. In such an embodiment, the tunable lens is set at a starting focal length $l_i$ by means of a driving signal at a starting voltage value $V_{p0}$, the focal length $l_i$ corresponding to the axial position $z_i$ and the laser beam is switched on, indicated by the focal spot 44 in FIG. 4. Upon switching on, the control unit drives a frequency variation in the control signal of the tunable lens from the starting voltage value $V_{p0}$ to a final voltage value $V_{p1}$ which determines a final focal length, $l_f$, corresponding to the final axial position $z_f$ of the focal spot of the laser beam.

FIG. 5b shows the switch-on time, V=5 Volts (supply voltage), and switch-off V=0, of the laser source. The laser source is switched off in the control signal ramp from $V_{p1}$ to $V_{p0}$ while it is switched on in the signal ramp from $V_{p0}$ to $V_{p1}$ when the beam is directed towards the cell. FIG. 5c is a representation of the number of optical pulses $N_{pulses}$ during the descent of the focal spot of the beam. The numerical values indicated are only provided as an example.

The electronic control unit, connected to the amplitude regulator of the control signal of the tunable lens, drives an amplitude variation from a first amplitude value to a second amplitude value. In the usual manners, the control unit, which comprises a microprocessor and a computer program for controlling the tunable focal length lens, is connected to an input device, such as a touch screen or a keyboard, through which an operator can enter the start and end voltage values, $V_{0i}$ and $V_{0f}$, of the control signal and the frequency value $f_{TL}$ of the signal.

With reference to the optoinjection apparatus in FIG. 1, an operating procedure of the optoinjection method according to an embodiment of the present invention comprises:
(i) placing a sample holder 18 on the microscope translation system 19, the sample holder containing a biological sample comprising a plurality of cells immersed in an extracellular solution containing exogenous material to be optoinjected;
(ii) with microscope lamp 21 on, translating the sample along axis z, by means of the translation system 19, to focus on the sample, and then translating the sample in plane (x, y) again by means of the translation system 19 (the laser source is off), observing the image of the sample to locate a cell of the plurality to be optoinjected, i.e. a recipient cell;
(iii) setting the coordinates x and y of the focal spot on a desired region of the recipient cell;
(iv) selecting a frequency-modulated electrical control signal of the tunable lens by selecting: frequency $f_{TL}$ of the signal so as to select the axial displacement speed of the focal spot (see Eq. (1)), a first voltage value $V_{0i}$ of the tunable lens control signal and a second voltage value $V_{0f}$ in which $V_{0i}$ and $V_{0f}$ correspond to axial position values $z_i$ and $z_f$, respectively; and thus to a traversing distance of the focal spot $\Delta z=(z_f-z_i)$;
(v) calculating the value $N_{pulses}/\mu m$, from this calculating the total number of pulses, $N_{pulses}$, of the laser beam during a (single) descent of the focal spot along distance $\Delta z$. If the beam pulse frequency varies during the displacement of the focal spot along $\Delta z$, the number of pulses is determined by Eq. (2);
(vi) selecting a number of cycles, $N_c \geq 1$, in which the descent of the focal spot of the laser is repeated on the same region of the cell, i.e. same coordinates (x,y) of point (iii) and with the same parameters set in steps (iv) and (v). With the number of cycles the total number of laser pulses that impinge the cell in the optoinjection procedure is determined, $N=N_c \cdot N_{pulses}$. In some embodiments, the number of cycles is an integer of between 1 and 5;
(vii) setting the frequency modulated control signal $f_{TL}$ to the voltage value $V_{0i}$;
(viii) controlling the switch on of the laser source;
(ix) continuously adjusting the voltage amplitude $V_0$ of the tunable lens control signal from the first value $V_{0i}$ to the second value $V_{0f}$, thus moving the focal spot of the laser beam along the traversing distance $\Delta z$;
(x) controlling the switching off of the laser source; and
(xi) if $N_c>1$, repeating steps (vii) to (x) a number $N_c$ of times.

The total number of laser pulses N can be calculated using the following equation:

$$N = N_c \cdot N_{pulses} = (\text{pulse frequency})/f_{TL} \qquad (3)$$

For some types of cell and/or exogenous material, an optoinjection cycle, $N_c=1$ can achieve an effective optoinjection. A number of cycles greater than 1 may increase the number of molecules injected in the same region of the cell and may be preferred in some cases of interest.

The method consistent with the present disclosure uses a sub-ns pulsed source which does not generate shockwaves in the sample and allows the use of a Gaussian beam with small focal spot, where relatively high optical forces are generated. In some preferred embodiments, a laser beam with not very high optical power may be used, for example of less than 30 µW.

While the present description refers to biological samples with living cells that represent applications of particular interest, the method according to the present description may also be applied to the optical injection into a recipient cell not in vivo, such as in the case of samples with cells in solution attached to a substrate.

EXAMPLE

Figure 6A:
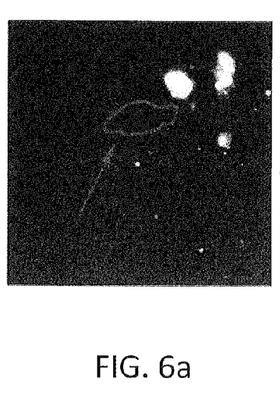
FIGS. 6a to 6f show a series of fluorescence microscopy images before, during and after the optoinjection of a laser beam, in an example of the present invention.

FIGS. 6a to 6f show a series of fluorescence microscope images captured before, during and after the optoinjection of a neuronal cell, respectively. Neuronal cells were incubated with a saline solution for cells containing fluorescent dyes FM1-43 in a glass Petri dish. The Petri dish had a base that was the substrate on which the cells, and in particular the recipient cell, were resting. Molecules FM1-43 are known to increase the quantum yield when they interact with the cell's membrane phospholipid layers, and it is therefore possible to detect the flow of the solution inside the cell when the membrane is pierced by the laser beam, since the molecules enter and interact with the membranes of the intracellular organelles. FIG. 6a is an image showing the target (recipient) cell highlighted by a contour indicated with an arrow, before the optoinjection. The white spots in FIG. 6a represent three dead cells that emit a fluorescent light saturated signal due to uncontrolled absorption by the dead cells of the dying molecules in the extracellular solution. Living cells have a low fluorescent light signal since their intact membrane does not allow the extracellular solution flow within them.

The experiment used an optoinjection apparatus of the type shown in FIG. 1. A laser source configured to emit a laser beam with 400 picosecond long pulses with a wavelength of 355 nm and a pulse repetition frequency of 1 kHz. The average optical power of the beam was 18 corresponding to an energy of nJ 18 per pulse. The laser was coupled to a tunable focal length optical system of the type shown in FIG. 1, comprising a tunable focal length lens EL-10-30 produced by Optotune, whose focal length may be varied from 50 mm to 125 mm. The tunable focal length lens was controlled by a control signal of the type shown in FIG. 5a, producing a displacement of the focal spot from 25 µm with respect to the substrate (corresponding to about 15 µm from the apical surface of the target cell, at the point of maximum height thereof) to 3 µm of axial distance from the surface of the substrate. The control signal frequency was of 6 Hz. A release of about 4-5 pulses per µm was obtained with these settings. The dichroic mirror arranged to receive the beam passed through the optical system was a mirror configured to reflect the optical beam to a wavelength of about 400 nm and transmit light at a longer wavelength. In this way, the microscope lamp light, which had a wavelength in the range of 400-500 nm, passes undisturbed through the dichroic mirror, like the fluorescent signal of molecules FM1-43, emitted at wavelengths of between 500 nm and 690 nm.

The beam reflected by the dichroic mirror enters the objective lens, a conventional water immersion objective for optical microscopy with magnification of 60× and NA=0.9, resulting in a focal spot of the laser beam having a diameter of about 500 nm in the plane (x, y) and about 800 nm in direction z.

The axial displacement speed was 125 µm/s.

Figure 6B:
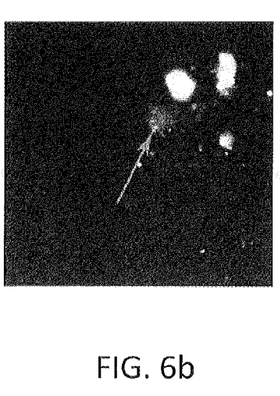
Figure 6C:
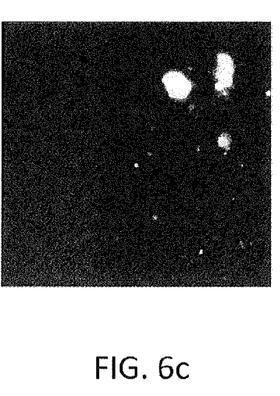
Figure 6D:
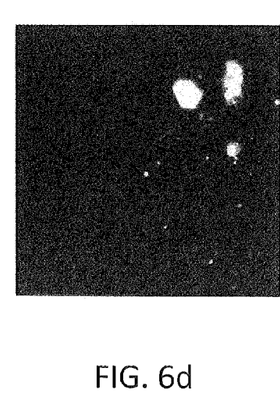
Figure 6E:
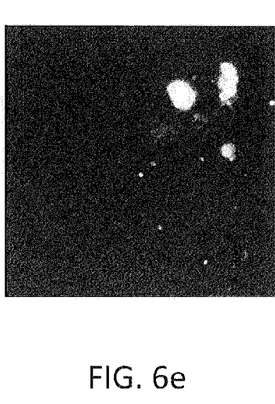
Figure 6F:
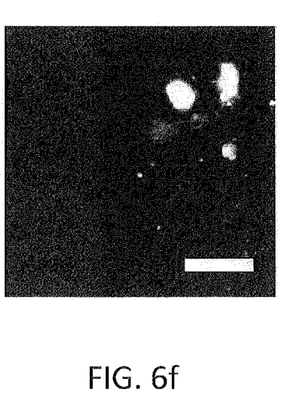

FIG. 6b shows the spatial-temporal position of the release of the optical beam pulse, indicated by an arrow.

When the cell is optically pierced, the extracellular solution enters the cell and the fluorescent dye interacts with the organelle membranes and compartments contained within the neuronal cell. The quantum yield of the molecules increases and therefore the fluorescent light signal emitted inside the cell. FIGS. 6c to 6f are fluorescence images of the cell after the completion of the optoinjection protocol, which were acquired at different times with 3 second intervals from one image to the other to visualize the increase in fluorescence emitted from within the cell.

Figure 7:
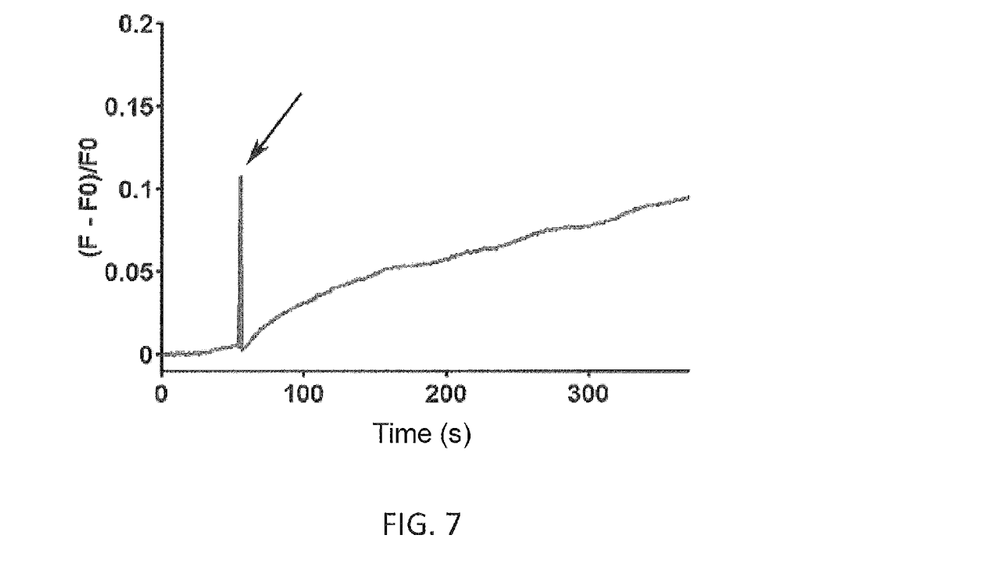
FIG. 7 is a graph showing the intensity of the fluorescence signal as a function of time, in which the signal is correlated to the entry of molecules into the cell during the optoinjection procedure of the example in FIGS. 6a to 6f.

FIG. 7 shows the average intensity, F, of fluorescent light over time, normalized to the average starting fluorescence value F0, calculated in the target cell area as a function of time. The intensity peak indicated with an arrow represents the laser switch on during a single descent step. In fact, in the experiment described in the present example, only one optoinjection cycle was carried out on the recipient cell.

However, a plurality of optical injection cycles may be set during the cyclical displacements of the focal spot. The optical injections may be made with a lower power laser beam so as to use lower average power of the laser and reduce photo-damage.

The invention claimed is:

1. A method for optoinjection of exogenous material into a recipient biological cell, wherein the cell comprises a cell membrane which encloses it, the method comprising:
   (a) placing a biological cell on a planar surface of a substrate, the cell having a basal surface resting on the planar surface of the substrate and an apical surface opposite the basal surface and in contact with a fluid solution which contains exogenous material;
   (b) transmitting a sub-ns pulsed laser beam through a variable convergence/divergence collimator, the collimator comprising a lens with focal length tunable by means of a variable amplitude control electrical signal;
   (c) directing the laser beam, having passed through the collimator, through an objective lens configured to focus the laser beam along an optical axis to a focal spot, the optical axis defining an axial direction substantially perpendicular to the planar surface of the substrate, such that the focal spot is positioned along the axial direction,
   (d) setting the electric control signal to a first amplitude value which defines a first focal length of the lens, corresponding to a first axial position z of the focal spot along the optical axis, wherein the first amplitude value of the control signal is selected such that the first axial position $z_i$ is above the apical surface of the cell at a first axial distance from the planar surface of the substrate; and
   (e) moving the focal spot towards the cell along the axial direction by continuously varying the electric control signal from the first amplitude value to a second amplitude value, the second amplitude value defining a second focal length corresponding to a second axial position $z_f$ of the focal spot, wherein the second amplitude value of the control signal is selected such that the second axial position is positioned inside the cell, at a second axial distance from the planar surface of the substrate, less than the first axial distance, such that the focal spot traverses the membrane of the cell during the descent of the focal spot towards the cell producing a pore in the membrane, which causes the fluid solution containing exogenous material to enter the cell.

2. The method according to claim 1, wherein the variable convergence/divergence collimator further comprises a second converging lens of fixed focal length, the second lens arranged with respect to the tunable focal length lens such that the laser beam traverses the second lens, in addition to the tunable focal length lens, before step (d).

3. The method according to claim 1 further comprising:
   (f) switching off the laser beam when the focal spot has reached the second axial position, and
   (g) setting the control signal, with the beam switched off, to the first amplitude value of the control signal such that the focal spot is positioned at the first axial position $z_i$ along the optical axis of the beam.

4. The method according to claim 3 further comprising, after step (g), switching on the laser beam and repeating the step (e).

5. The method according to claim 1, wherein the electric control signal of the tunable focal length lens is an analog electric signal.

6. The method according to claim 1, wherein the control signal of the tunable focal length lens is an analog electric signal frequency modulated at a frequency $f_{TL}$ that determines the speed of axial displacement of the focal spot, $v_{fs}$, during its descent from the first axial position to the second axial position, according to the relationship $v_{fs}=2(z_f-z_i)f_{TL}$.

7. The method according to claim 6, wherein the speed of axial displacement of the focal spot is from 10 µm/s to 500 µm/s.

8. The method according to claim 1, wherein the focal spot has a size along the axial direction comprised between 300 nm and 1000 nm.

9. The method according to claim 1, wherein the tunable focal length lens is a lens of variable shape that can be electrically controlled by means of an actuator controlled by the variable amplitude electric control signal.

10. The method according to claim 1, wherein the travel axial distance of the focal spot of the laser beam $\Delta z=(z_f-z_i)$ is comprised between 20 µm and 100 µm.

11. The method according to claim 6, wherein the speed of axial displacement of the focal spot is from 80 to 150 µm/s.

* * * * *